United States Patent
Mills et al.

[11] Patent Number: 6,165,005
[45] Date of Patent: *Dec. 26, 2000

[54] PATIENT CABLE SENSOR SWITCH

[75] Inventors: Michael A. Mills, Mission Viejo, Calif.; Thomas J. Gerhardt, Littleton, Colo.

[73] Assignee: Masimo Corporation, Irvine, Calif.

[*] Notice: This patent is subject to a terminal disclaimer.

[21] Appl. No.: 09/456,232

[22] Filed: Dec. 7, 1999

Related U.S. Application Data

[63] Continuation of application No. 09/044,703, Mar. 19, 1998, Pat. No. 5,997,343.

[51] Int. Cl.[7] .................................................. H01R 3/00
[52] U.S. Cl. .................................................... 439/489
[58] Field of Search .................................. 439/489, 188, 439/160, 353, 374, 352, 378; 200/51.09

[56] References Cited

U.S. PATENT DOCUMENTS

| | | |
|---|---|---|
| 4,684,245 | 8/1987 | Goldring . |
| 5,249,576 | 10/1993 | Goldberger et al. . |
| 5,287,853 | 2/1994 | Vester et al. . |
| 5,387,122 | 2/1995 | Goldberger et al. . |
| 5,807,247 | 9/1998 | Merchant et al. . |
| 5,997,343 | 12/1999 | Mill et al. ............................ 439/489 |

*Primary Examiner*—Khiem Nguyen
*Assistant Examiner*—J. F. Duverne
*Attorney, Agent, or Firm*—Knobbe, Martens, Olson & Bear, LLP

[57] ABSTRACT

A sensor switch located in a patient cable adapts an incompatible sensor to a monitor in a pulse oximetry system. The sensor switch is particularly suited to adapting sensors to a monitor that utilizes an open-circuit detector to determine a no-sensor condition. A compatible sensor short-circuits the inputs to the open-circuit detector to indicate sensor presence. An incompatible sensor has such no short-circuit feature and fails to work on such a monitor. An incompatible sensor attached to a sensor connector at one end of the patient cable, however, actuates the sensor switch. The sensor switch, in turn, short-circuits the open-circuit detector inputs when the monitor is attached to a monitor connector at the opposite end of the patient cable. Thus, the sensor switch simulates the presence of a compatible sensor to the monitor.

9 Claims, 8 Drawing Sheets

PATIENT CABLE SENSOR SWITCH

This application is the continuation of the patent application Ser. No. 09/044,703, filed Mar. 19, 1998 is now U.S. Pat. No. 5,997,343.

BACKGROUND OF THE INVENTION

Oximetry is the measurement of the oxygen status of blood. Early detection of low blood oxygen is critical in the medical field, for example in critical care and surgical applications, because an insufficient supply of oxygen can result in brain damage and death in a matter of minutes. Pulse oximetry is a widely accepted noninvasive procedure for measuring the oxygen saturation level of arterial blood, an indicator of oxygen supply. A pulse oximetry system consists of a sensor attached to a patient, a monitor, and a cable connecting the sensor and monitor.

Conventionally, a pulse oximetry sensor has both red and infrared LED emitters and a photodiode detector. The sensor is typically attached to an adult patient's finger or an infant patient's foot. For a finger, the sensor is configured so that the emitters project light through the fingernail and into the blood vessels and capillaries underneath. The photodiode is positioned at the fingertip opposite the fingernail so as to detect the LED emitted light as it emerges from the finger tissues.

The pulse oximetry monitor determines oxygen saturation by computing the differential absorption by arterial blood of the two wavelengths emitted by the sensor. The monitor alternately activates the sensor LED emitters and reads the resulting current generated by the photodiode detector. This current is proportional to the intensity of the detected light. The monitor calculates a ratio of detected red and infrared intensities, and an arterial oxygen saturation value is empirically determined based on the ratio obtained. The monitor contains circuitry for controlling the sensor, processing sensor signals and displaying a patient's oxygen saturation, heart rate and plethysmographic waveform. A pulse oximetry monitor is described in U.S. Pat. No. 5,632,272 assigned to the assignee of the present invention.

The patient cable provides conductors between a first connector at one end, which mates to the sensor, and a second connector at the other end, which mates to the monitor. The conductors relay the emitter drive currents from the monitor to the sensor emitters and the photodiode detector signals from the sensor to the monitor.

Figure 1:
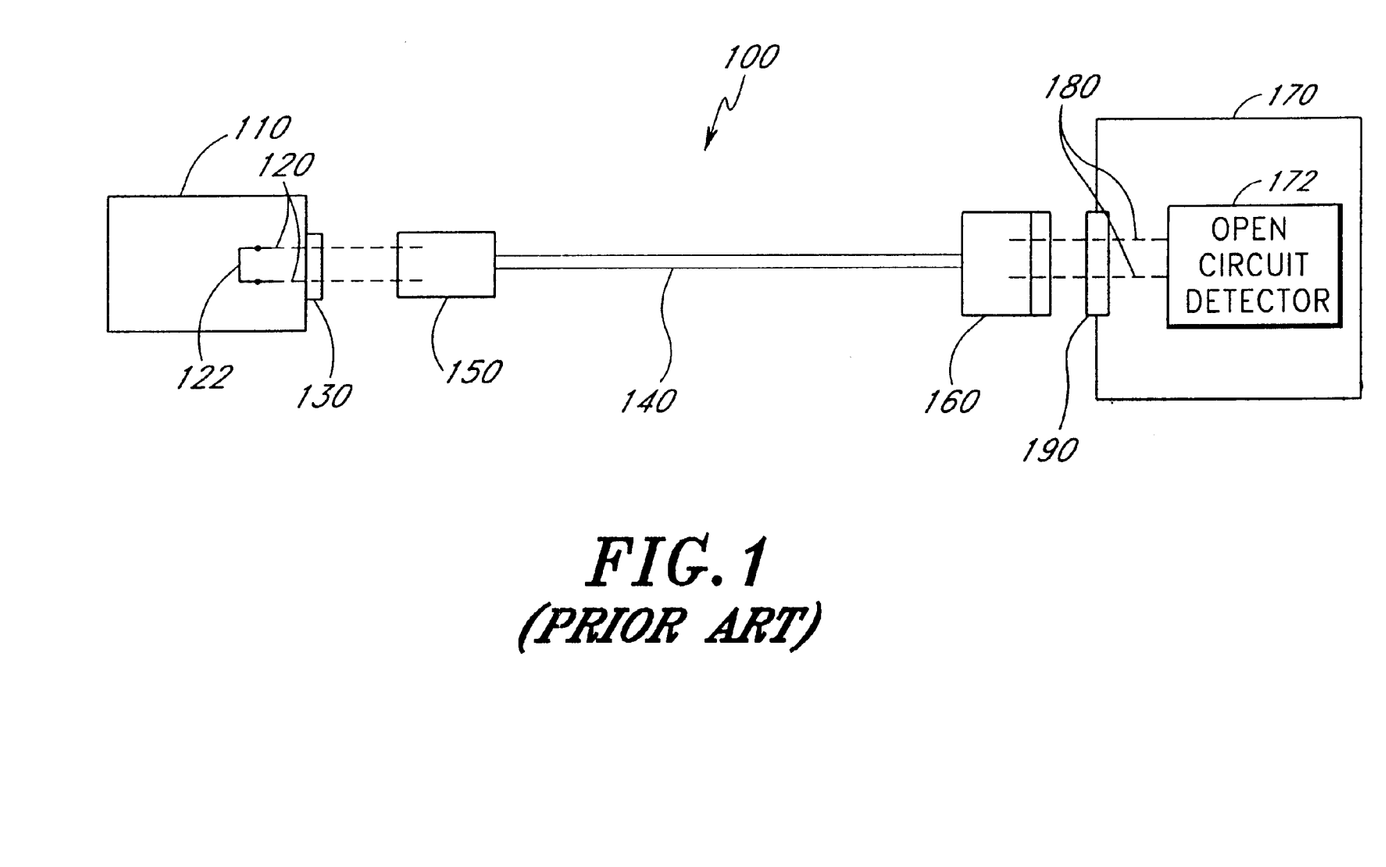
FIG. 1 is a block diagram of a prior art sensor and a corresponding pulse oximetry monitor.

The patient cable conductors may also relay information to the monitor regarding sensor status. For example, FIG. 1 shows a prior art pulse oximetry system 100 that detects whether a sensor 110 is connected to a monitor 170, either directly or through a patient cable 140. The sensor has a conductor pair 120 (shown dashed) that corresponds to pinouts on a sensor connector 130. The monitor 170 also has a conductor pair 180 (shown dashed) that corresponds to pinouts on a monitor connector 190. The patient cable 140 mates with the sensor 110 at one end and the monitor 170 at the other end, so that the sensor conductor pair 120 becomes electrically connected to the monitor conductor pair 180. A short-circuit conductor 122 connects the sensor conductor pair 120 together at the sensor 110. An open circuit detector 172 within the monitor 170 senses the conductance across the monitor conductor pair 180. When the sensor 110 is plugged into the patient cable 140, the sensor conductor pair 120 is connected to the monitor conductor pair 180, and the conductance measured by the open-circuit detector indicates the presence of the short-circuit conductor 122. When the sensor 110 is unplugged from the patient cable 140, the sensor conductor pair 120 is disconnected from the monitor conductor pair 180, and the conductance measured by the open-circuit detector 172 indicates an open-circuit. Hence, the combination of the short-circuit conductor 122 and the monitor open-circuit detector 172 functions to detect a no-sensor condition. This is a useful indicator for the monitor signal processor, which can distinguish between a sensor malfunction and a no-sensor condition, providing a display to the user accordingly.

SUMMARY OF THE INVENTION

A drawback to conventional pulse oximetry systems is the lack of standardization of the sensor and the monitor. Unless the same company manufactures the sensor and the monitor, it is unlikely that these two components can be connected as a functioning pulse oximetry system. One such incompatibility regards a monitor's capability to detect a "no-sensor" condition. Described above with respect to FIG. 1 is a sensor configuration that allows a compatible monitor to determine when a sensor is connected by sensing a short-circuit between two sensor conductors. Some sensor configurations, however, are intended for connection to monitors that do not distinguish between a no-sensor condition and a sensor malfunction. For example, a sensor may be connected to the monitor, but fails to respond to monitor drive signals. Other sensors, although providing compatible monitors with a method of detecting a no-sensor condition, do so with entirely different sensor configurations than described in FIG. 1. For example, a sensor may provide a resistive element, the value of which indicates to the monitor not only sensor presence, but such information as sensor type, LED wavelength and sensor manufacturer. Thus, a monitor that specifically looks for an open-circuit to indicate a no-sensor condition will not function with an incompatible sensor that is configured with a different indicator or no indicator of sensor presence. A sensor switch incorporated within a patient cable according to the present invention allows such an incompatible sensor to function with a monitor that senses an open-circuit to determine a no-sensor condition.

One aspect of the present invention is an adapter for connecting a sensor to a pulse oximetry monitor. The adapter comprises a sensor connector and a monitor connector in communications with the sensor connector. The adapter also comprises an adapter element having a first state when the sensor is attached to the sensor connector and a second state when the sensor is not attached to the sensor connector. The adapter element is in communication with the monitor connector so that, when the monitor is connected to the monitor connector, the monitor can detect the second state. In one embodiment, the adapter element is a switch having a first position corresponding to the first state and a second position corresponding to the second state. The switch may be integral to the sensor connector. The switch further may be normally open and actuated to a closed position by the connection of the sensor to the sensor connector. In a specific embodiment, the switch comprises a switch contact and a plurality of spring contacts. Each spring contact has an unflexed position separated from the switch contact and a flexed position touching the switch contact. The switch contact electrically connects the spring contacts in the flexed position.

Another aspect of the present invention is a method of adapting a sensor to a pulse oximetry monitor. The method comprises the step of providing a sensor connector that is in communications with a monitor connector. The method also comprises the step of creating a signal at the monitor connector in response to the attachment of the sensor to the sensor connector so that the monitor can determine a no-sensor condition when attached to the monitor connector. In one embodiment, the creating step comprises actuating a switch to short together a plurality of conductors at the monitor connector. The conductors correspond to inputs to an open circuit detector in the monitor.

Yet another aspect of the present invention is a sensor adapter having a sensor connector and a monitor connector. The sensor adapter comprises a sensing means for determining that a sensor is attached to the sensor connector and a signaling means for communicating between the sensing means and the monitor connector so that a monitor attached to the monitor connector detects a no-sensor condition.

DETAILED DESCRIPTION OF THE PREFERRED EMBODIMENTS

Figure 2:
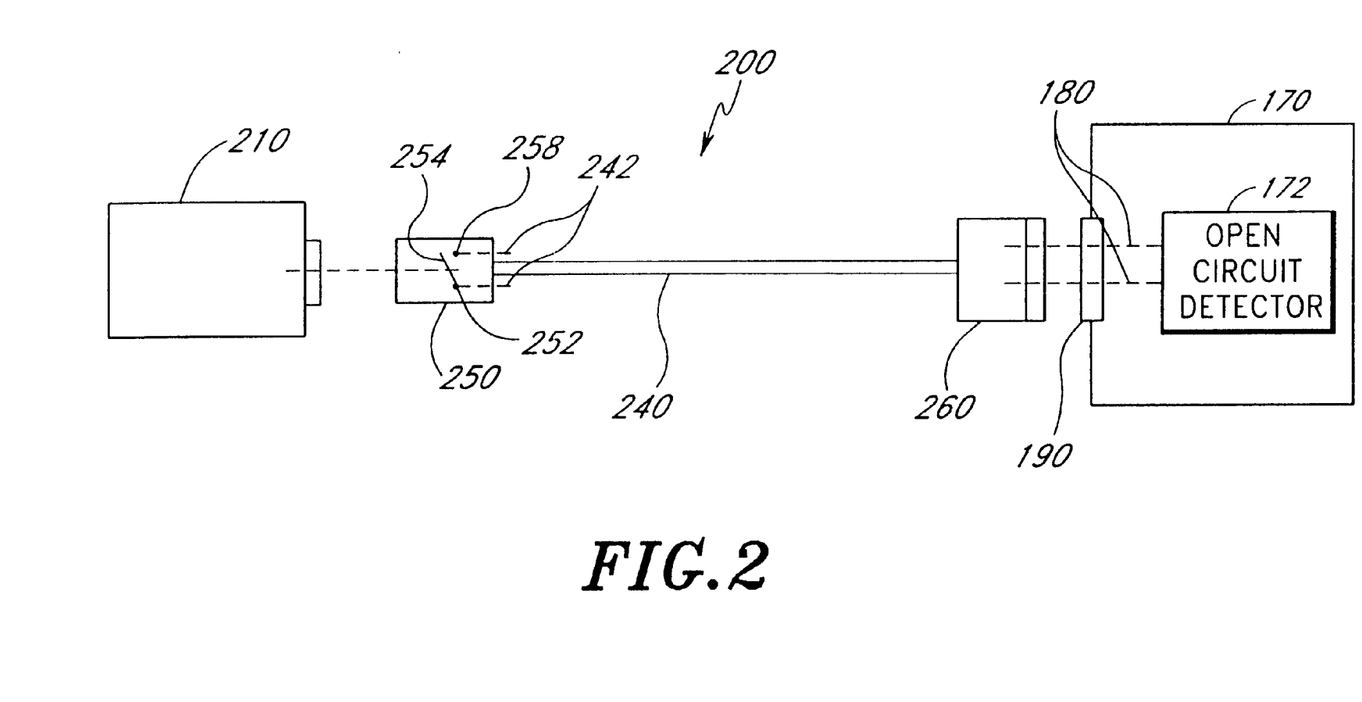
FIG. 2 is a block diagram of a patient cable connector having a sensor switch according to the present invention.

FIG. 2 shows a block diagram of a pulse oximetry system 200 having an adapter patient cable 240 for interconnecting an incompatible sensor 210 to a monitor 170. The sensor 210 attaches to a sensor connector 250 at one end of the patient cable 240, and the monitor 170 attaches to a monitor connector 260 at the other end of the patient cable 240. The monitor 170, as described above with respect to FIG. 1, has a conductor pair 180 (shown dashed) that corresponds to pinouts on a monitor connector 190. The monitor 170 also has an open circuit detector 172 that senses the conductance across the monitor conductor pair 180. The sensor 210 is incompatible in that, unlike a compatible sensor 110 (FIG. 1) it does not have a short-circuit conductor 122 (FIG. 1). When attached to the monitor 170 with a conventional patient cable 140 (FIG. 1), the incompatible sensor 210 does not provide a low conductance path between the monitor conductor pair 180. The monitor 170 detects an open circuit 172 and assumes a no-sensor condition. As a result, the monitor will not function with the sensor 210.

In order to adapt the incompatible sensor 210 to the monitor 170, a sensor switch 252 is incorporated into the sensor connector 250 of the adapter patient cable 240. The sensor switch 252 has a normally open position 254 (depicted) and a closed position 258. The switch 252 is located between a cable conductor pair 242. The cable conductor pair 242 corresponds to pinouts on the monitor connector 260, which connect to the open circuit detector 172 through the corresponding monitor conductor pair 180.

The open-circuit detector 172 functions as described above with respect to FIG. 1. Thus, the cable conductor pair 242 appears as an open circuit when no sensor is attached to the sensor connector 250 and as a short circuit when the sensor 210 is attached to the sensor connector 250.

To accomplish this function, the sensor switch 252 is actuated when the sensor is attached to the sensor connector 250, moving the switch 252 from the normally open 254 to the closed position 258. In the closed position 258, the sensor switch 252 provides a low conductance path between the monitor conductors 180, which the open circuit detector 172 interprets as an attached compatible sensor. As a result, the adapter patient cable 240, along with the incorporated sensor switch 252, allows the monitor 170 to function with the incompatible sensor 210.

Figure 3A:
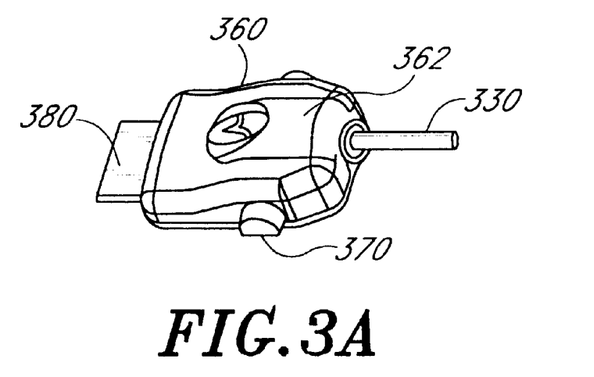
FIG. 3 is a perspective view of a patient cable illustrating the sensor-end and monitor-end cable connectors.
Figure 3B:
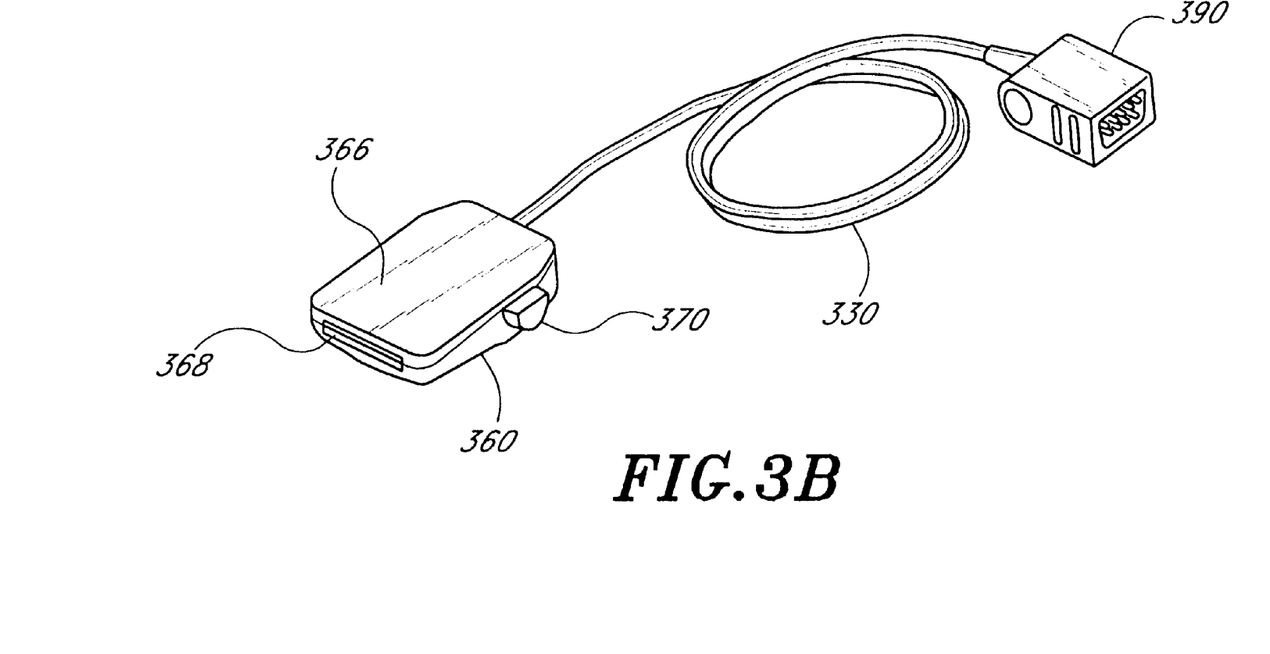

FIG. 3 depicts an embodiment of the adapter patient cable for attaching an incompatible sensor to a monitor. The patient cable 300 has a cable portion 330 with a sensor connector 360 at one end and a monitor connector 390 at the other end. The cable portion 330 has conductors that connect on one end to contacts within the sensor connector 360 and on the other end to pins of the monitor connector 390. In this particular embodiment, the monitor connector 390 is depicted as a D-type connector. The sensor connector 360 includes a top case 362 and a bottom case 366. The top case 362 and bottom case 366 together form an insertion slot 368 that accepts a sensor plug 380. Although the sensor plug 380 is shown in FIG. 3 as a blank, in use, this plug 380 is a portion of the sensor or is attached to the end of a sensor cable. The sensor connector 360 also includes a sensor plug release mechanism actuated by release buttons 370. The sensor connector 360 and the sensor switch contained therein are described in more detail below.

Figure 4:
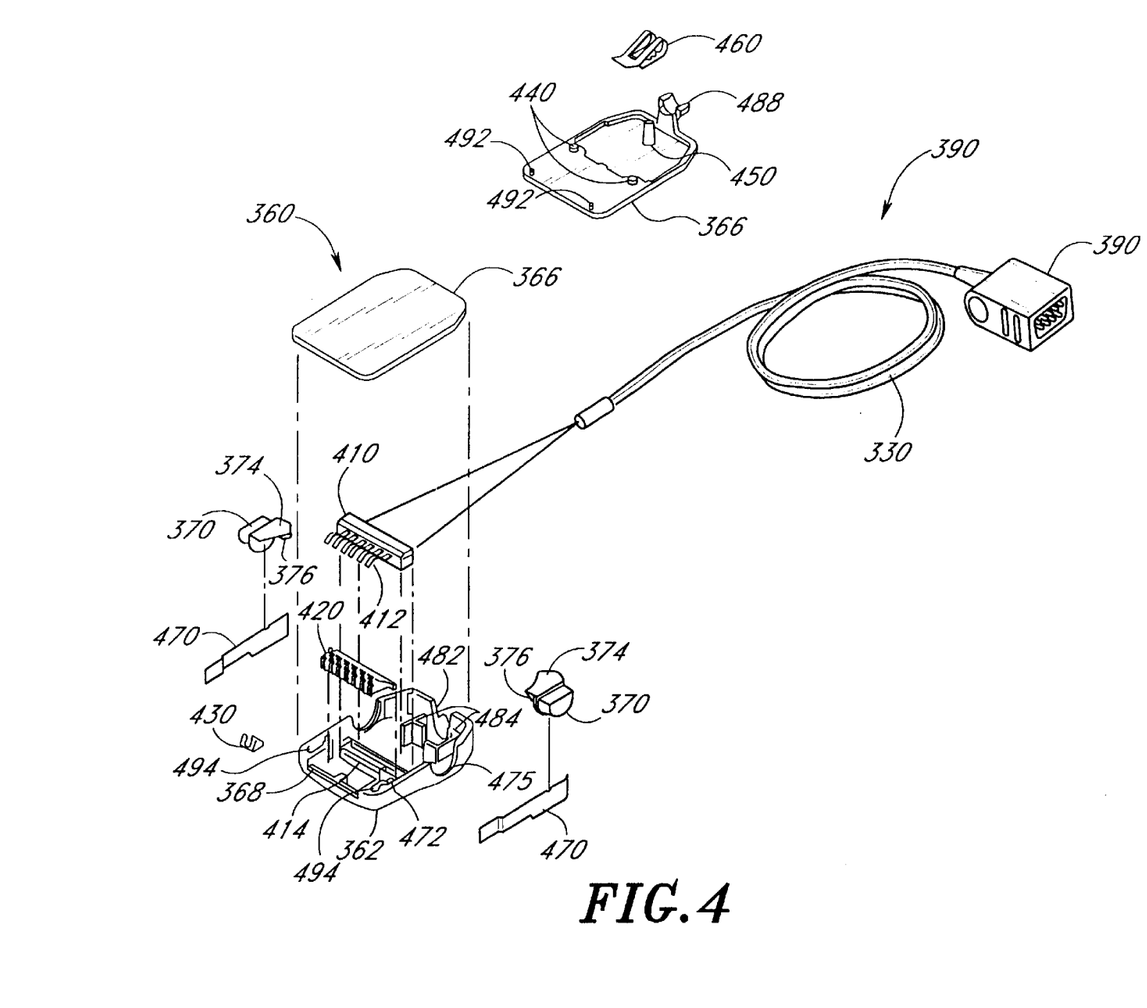
FIG. 4 is an exploded diagram of a patient cable connector incorporating a sensor switch.

FIG. 4 depicts an exploded view of the sensor connector 360 viewed into the top case 362. The sensor connector 360 contains sensor switch components, which include a contact block 410, a contact stop 420 and a switch contact 430. The contact block 410 contains multiple spring contacts 412. Each spring contact 412 may be connected to one or more wires from the cable 330. The spring contacts 412 are advantageously made of beryllium copper alloy or like material having a high strength to modulus of elasticity. This feature allows the spring contacts 412 to flex without yielding, i.e. failing to return to their original form and position. The contact block 410 is mounted in a contact holder 414 of the top case 362. When a sensor plug 500 (FIG. 5) is inserted into the insertion slot 368, the spring contacts 412 flex from a normal position to a position proximate the contact stop 420. The contact stop 420 prevents the spring contacts 412 from shorting against conductive portions of the top case 362 and has fingers and grooves that protect each spring contact 412 from sideways deformation. Mounted on the contact stop 420 is a switch contact 430. When the sensor plug 500 moves the spring contacts 412 proximate the contact stop 420, two of the spring contacts 412 touch the switch contact 430, creating a short-circuit between a corresponding pair of conductors in the cable 330. The operation of this sensor switch is described in further detail below.

Figure 5A:
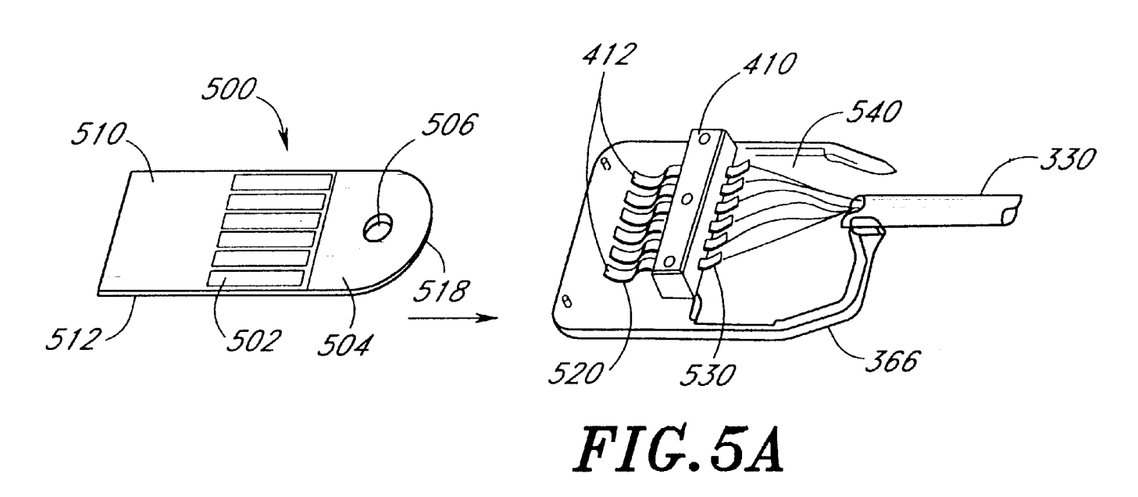
FIG. 5 is a perspective view of a portion of a patient cable connector and a corresponding sensor plug.
Figure 5B:
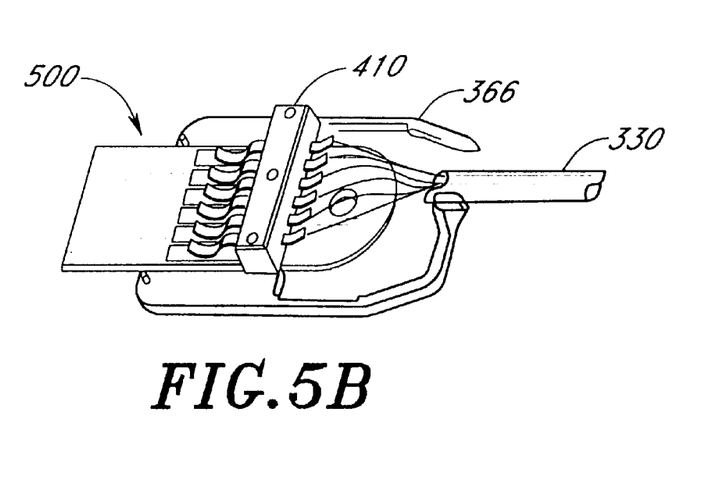

The sensor connector 360 also contains components and features that facilitate the insertion and retention of the sensor plug 500 (FIG. 5). The bottom case 366 has elevation posts 440 that allow the sensor plug 500 to be placed into the insertion slot 368 and pushed beyond the contact block 410 along the inside face of the bottom case 366 until the sensor plug 500 contacts a stop bar 450. At the stop bar 450, the sensor plug 500 is held in place with a tab catch spring 460.

In addition, the sensor connector 360 contains components that provide for the release of the sensor plug 500 (FIG. 5), which include release buttons 370 and spring members 470. The release buttons 370 are located in release button slots 475 so that the release buttons 375 protrude from the sides of the top case 362. The spring members 470 are located in inner side slots 472 of the top case 362.

Further, the sensor connector 360 contains features that provide for the positioning, connection and retention of the cable portion 330 of the patient cable 300. These features include a cable guide 482 and cable holders 484 molded into the top case 362 and a cable mount 488 molded into the bottom case 366. The cable 330 is secured between the cable guide 482 and the cable mount 488 when the top case 362 and the bottom case 366 are bonded together, which holds the cable 330 in position and provides some cable stress relief. The cable holders 484 are L-shaped members offset from each other. The conductors of the cable 330 are woven between the cable holders 484 to provide additional cable stress relief In one embodiment, the cable 330 is bonded in place with epoxy.

The top case 362 and bottom case 366 are advantageously made of plastic, resin or the like. When the top case 362 and bottom case 366 are attached together, the cable 330, contact block 410, contact stop 420 and release mechanisms 370, 470 are secured in place. The top case 362 and bottom case 366 are attached so that edges are aligned. The inner side of the top case 362 has positioning apertures 494 which function with the positioning posts 492 on the bottom case 366 to facilitate alignment of the top case 362 and the bottom case 366. In one embodiment, the top case 362 is glued or sonically welded to the bottom case 366 along all edges.

FIG. 5 illustrates the sensor plug 500, shows the relative positions of the contact block 410, the bottom case 366 and the sensor plug 500, and depicts the cable 330, cable wiring 540 and connection of the cable wiring 540 to contact tabs 530 of the spring contacts 412. The sensor plug 500 is the connector portion of a pulse oximetry sensor (not shown). The sensor plug 500 has electrical contacts 502, a sensor tab 504 and a locking hole 506. The sensor plug 500 is made from a two-piece assembly of a polymer flex circuit 510 bonded to a molded plastic portion 512 which also forms the tab 504. The contacts 502 are made by etching of a copper coating or other metallic coating on one side of the polymer 510.

The sensor plug 500 is pushed into the insertion slot 368 of the sensor connector 360 (FIG. 3). As the sensor plug 500 is inserted, the leading edge 518 engages the spring contacts 412, lifting the spring contacts 412 in a direction away from the bottom case 366. As described with respect to FIG. 7 below, this lifting of the spring contacts 412 causes two of the spring contacts 412 to touch the switch contact 430 (FIG. 4), actuating the sensor switch. As insertion of the sensor plug 500 continues, the sensor tab 504 slides between the contact block 410 and the bottom case 366 as the curved portion 520 of the spring contacts 412 engage the sensor plug contacts 502. When fully inserted, the spring contacts 412 and the plug contacts 502 remain electrically connected. The spring contacts 412 protrude on one side of the contact block 410 to form contact tabs 530. The cable 330 is positioned so that cable wires 540 can be soldered to the contact tabs 530. Thus, signals can be transmitted between the sensor and the monitor via the cable wires 540, contact tabs 530, spring contacts 412 and sensor contacts 502.

Figure 6A:
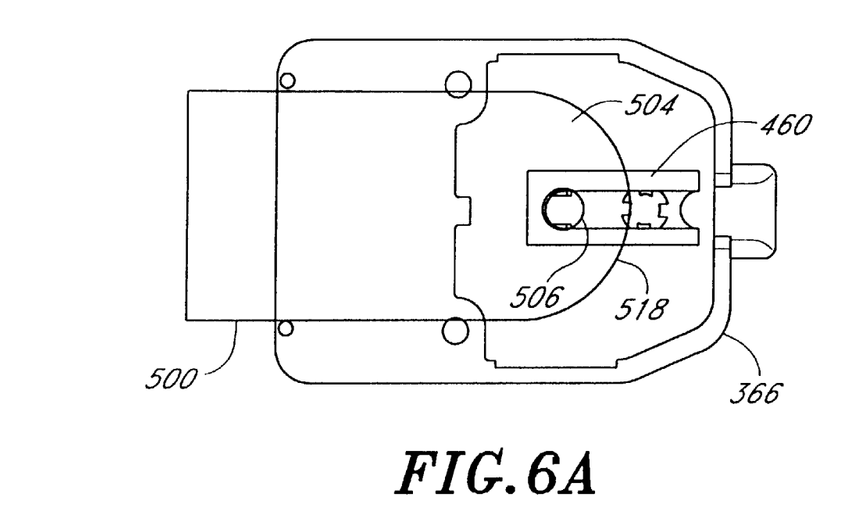
FIG. 6 is a plan view of a portion of the patient cable connector illustrating a sensor tab catch.
Figure 6B:
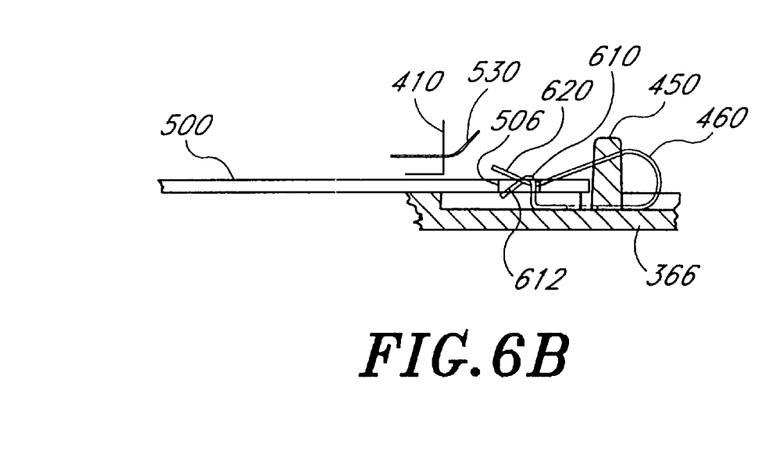

FIG. 6 illustrates detail of the tab catch spring 460 and the corresponding retention of the sensor tab 504. The tab catch spring 460 has tab catch portion 610 and a retention portion 620 and is mounted on the stop bar 450. As the sensor plug 500 is inserted into the insertion slot 368 of the sensor connector 360 (FIG. 3), the sensor tab 504 slides flush along the surface of the bottom case 366 until the leading edge 518 abuts the tab catch 610. As insertion of the sensor plug 500 continues, the sensor tab 504 is directed away from the bottom case 366 by the sloped portion 612 of the tab catch 610. This causes the sensor tab 504 to lift the retention portion 620 and slide over the tab catch 610. Insertion is complete as the leading edge 518 of the sensor tab 504 rests against the stop bar 450, and the tab catch 610 is positioned inside the locking hole 506. It should be understood that an indentation in the sensor tab 504 could replace the locking hole 506. The sensor plug 500 is firmly fixed in place when fully inserted into the sensor connector. This is due to the combination of the downward force of the retention portion 620 on the sensor tab 504, the position of the tab catch 610 within the locking hole 506, and the position of the leading edge 518 against the stop bar 450. This reduces noise, which may be generated from sliding of the sensor contacts 502 with respect to the spring contacts 412 (FIG. 5).

As depicted in FIGS. 4 and 6, the tab catch 610 as described above prevents the sensor plug 500 from being removed from the sensor connector 360 unless released. To release the sensor plug 500 from the sensor connector 360, the user pushes both release buttons 370 into the top case 362. When the release buttons 370 are pushed, lift tabs 374 raise the sensor plug 500 off of the tab catch 610. The lift tabs 374 are wedge shaped, i.e. the thickness of a lift tab 374 is smallest on the inside edge and gradually increases towards the release button 370. When the release buttons are pressed, they force the thicker portions of the lift tabs 374 to wedge between the inner face of the bottom case 366 and exert pressure on the sensor plug 500 to lift the sensor tab 504 off the tab catch 610.

At the same time the sensor plug 500 is raised off the tab catch 610, push tabs 376 press the sensor plug 500 away from the stop bar 450. As the release buttons 370 are depressed, the leading edge of each push tab 376 comes in contact with the sensor tab leading edge 518. As further depression of the release buttons 370 occurs, the push tabs 376 move together against the "U" shape of the leading edge 518, pushing the sensor plug 500 away from the stop bar 450. This pushing motion moves the locking hole 506 away from the tab catch 610, thereby preventing the tab catch 610 from re-engaging the locking hole 506 when the release buttons 370 are released. This allows a user to merely pull the sensor plug 500 from the sensor connector 360 after the release buttons 370 have been depressed.

Figure 7A:
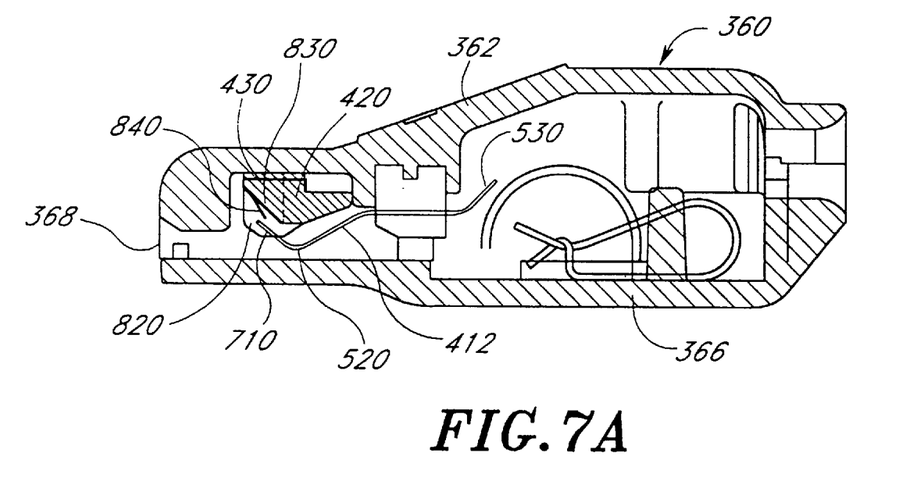
FIG. 7 is a detailed cross-sectional view and plan view of the patient cable connector incorporating a sensor switch.
Figure 7B:
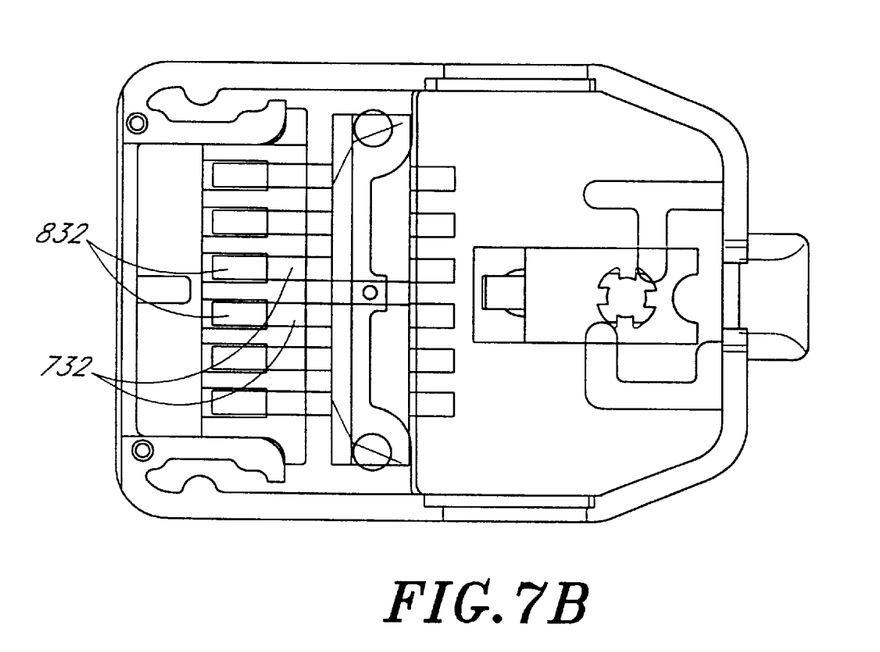
Figure 8:
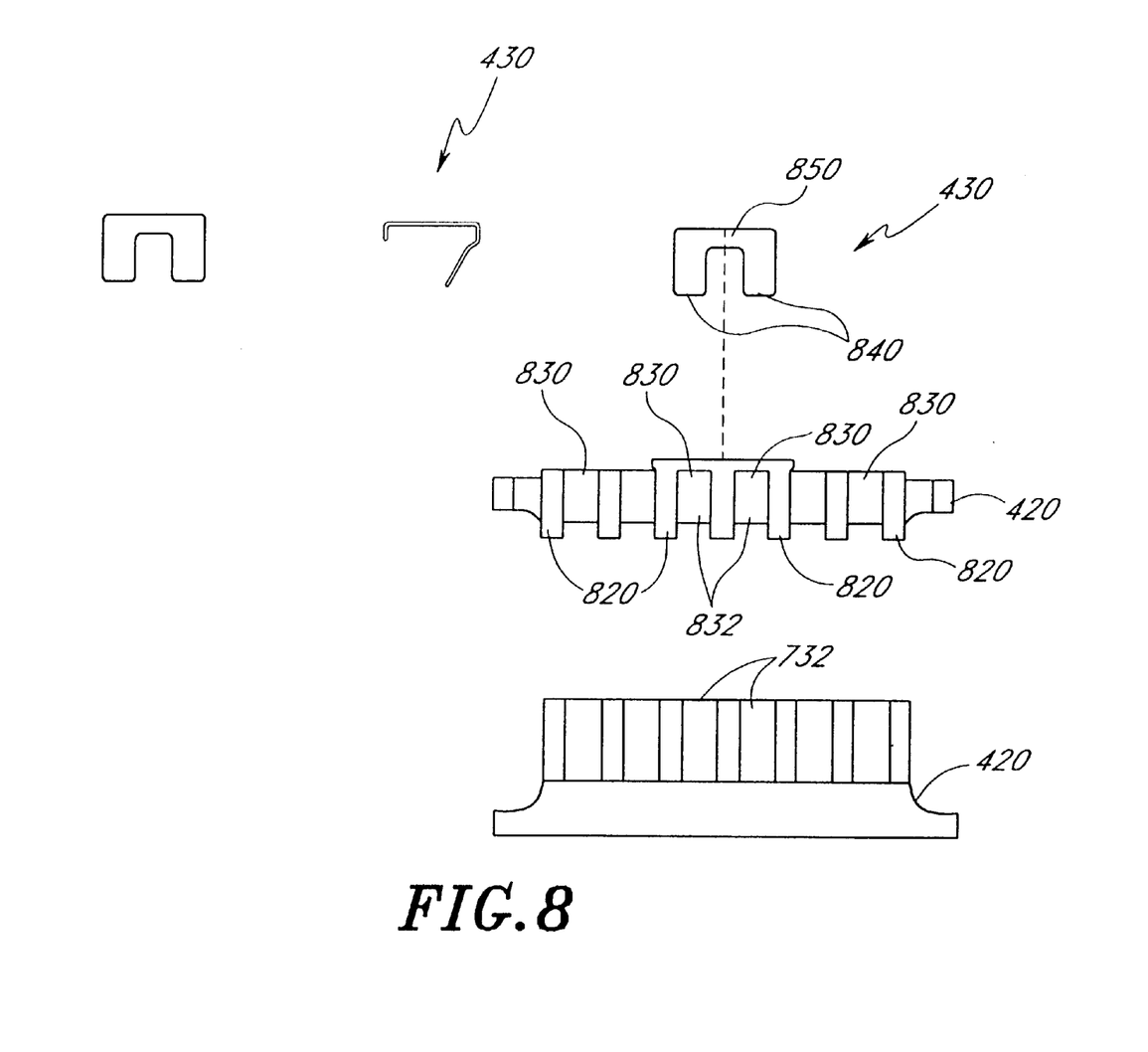
FIG. 8 is a plan view of the contact stop and switch contact portions of the sensor switch.

FIG. 7 depicts the details of the spring contact 412 and switch contact 430 portions of the sensor switch according to the present invention. FIG. 8 provides further details and relative positions of the contact stop 420 and the switch contact 430 portions of the sensor switch. As shown in FIGS. 7 and 8, each spring contact 412 has a tab portion 530, a curved portion 520 and a end portion 710. As described above, the curved portion 520 makes an electrical connection with sensor plug contacts 502 (FIG. 5). The spring contact tabs 530 provide connection to patient cable wires 540 (FIG. 5). Without an applied force, the spring contacts 412 each maintain a normal position (depicted) between fingers 820 of the contact stop 420 and spaced from grooves 830 of the contact stop 420. As described above, when the sensor plug 500 (FIG. 5) is connected through the insertion slot 368 of the sensor connector 360, the sensor plug 500 forces the spring contacts 412 to a position away from the bottom case 366. With the sensor plug 500 inserted, the spring contacts 412 are each forced to a position proximate the contact stop grooves 830.

A switch contact 430 is mounted on the contact stop 420 so that the switch prong portions 840 of the switch contact 430 are positioned within two center grooves 832. With the sensor plug inserted, the end portion 710 of two center spring contacts 732 make an electrical connection with the switch prongs 840 when forced to a position proximate the grooves 830. The switch prongs 840 are biased slightly away from the grooves 830 to facilitate this electrical connection with the contact end portions 710 of the center spring contacts 732. A shorting bar portion 850 of the switch contact 430 provides a low conductance path between the switch prongs 840 and, hence, the center spring contacts 732. Thus, when the sensor plug 500 (FIG. 5) is inserted into the insertion slot 368, the two wires 540 (FIG. 5) connected to the tab portion 530 of the center spring contacts 732 provide outputs at the monitor connector 390 (FIG. 4) that are shorted together. Hence, the action of the sensor switch as described above provides a no-sensor indicator for a monitor having an open circuit detector 172 (FIG. 2) that senses these sensor switch outputs.

The patient cable sensor switch has been disclosed in detail in connection with various embodiments of the present invention. These embodiments are disclosed by way of examples only and are not to limit the scope of the present invention, which is defined by the claims that follow. One of ordinary skill in the art will appreciate many variations and modifications within the scope of this invention.

What is claimed is:

1. An adapter for connecting a sensor to a pulse oximetry monitor, said adapter comprising:
   a sensor connector;
   a monitor connector in communications with said sensor connector; and
   an adapter element having a first state when said sensor is attached to said sensor connector and a second state when said sensor is not attached to said sensor connector, said adapter element in communication with said monitor connector so that, when said monitor is connected to said monitor connector, said monitor can detect said second state.

2. The adapter of claim 1 wherein said adapter element is a switch having a first position corresponding to said first state and a second position corresponding to said second state.

3. The adapter of claim 2 wherein said switch is integral to said sensor connector.

4. The adapter of claim 3 wherein said first state is a normally open state and said switch is actuated to said second state of a closed position by the connection of said sensor to said sensor connector.

5. The adapter of claim 4 wherein said switch comprises:
   a switch contact; and
   at least two spring contacts, each having an unflexed position separated from said switch contact and a flexed position touching said switch contact, said switch contact electrically connecting said spring contacts in said flexed position.

6. A method of adapting a sensor to a pulse oximetry monitor comprising the steps of:
   providing a sensor connector in communications with a monitor connector; and
   creating a signal at said monitor connector in response to the attachment of said sensor to said sensor connector so that said monitor can determine a no-sensor condition when attached to said monitor connector.

7. The method of claim 6 wherein said creating step comprises actuating a switch to short together a plurality of conductors at said monitor connector.

8. The method of claim 7 wherein said conductors correspond to inputs to an open circuit detector in said monitor.

9. A sensor adapter having a sensor connector and a monitor connector comprising:
   a sensing means for determining that a sensor is attached to said sensor connector; and
   a signaling means for communicating between said sensing means and said monitor connector so that a monitor attached to said monitor connector detects a no-sensor condition.

* * * * *